United States Patent [19]

Zeuthen et al.

[11] Patent Number: 4,816,441
[45] Date of Patent: Mar. 28, 1989

[54] PEPTIDES AND COMPOSITIONS

[75] Inventors: Jesper Zeuthen, Virum; Lars Thim, Gentofte; Niels P. H. Moller, Lyngby, all of Denmark

[73] Assignee: Novo Industri A/S, Denmark

[21] Appl. No.: 930,481

[22] Filed: Nov. 14, 1986

[30] Foreign Application Priority Data

Nov. 15, 1985 [DK] Denmark ............................ 5282/85

[51] Int. Cl.⁴ ...................... A61K 37/02; C07K 7/10; C07K 7/08; C07K 7/06
[52] U.S. Cl. ...................................... 514/12; 530/324; 530/325; 530/326; 530/327; 530/328; 530/329; 530/330
[58] Field of Search ............... 530/350, 324, 325, 326, 530/327, 328, 329, 330; 514/12

[56] References Cited

PUBLICATIONS

Computer Printout.
Chem. Abstr., vol. 85 (1976), 88835.
Chem. Abstr., vol. 98 (1983), 210813.
Chem. Abstr., vol. 107 (1987, 35293.
Uhlén et al., *J. Biol. Chem.* 259(3): 1695–1702, (1984).
Sjodahl, *Eur. J. Biochem.* 73: 343–351 (1977).
Guss et al., *Eur. J. Biochem.* 153: 579–585 (1985).
Ghetie et al., *Mol. Immunol.* 23(4): 377–384 (1986).
Laky et al., *Mol. Immunol.* 22(11): 1297–1302 (1985).
Moks et al., *Eur. J. Biochem.* 156: 637–643 (1986).
Ainsworth et al., *Cancer* 61: 1495–1500 (1988).

*Primary Examiner*—Delbert R. Phillips
*Attorney, Agent, or Firm*—Saidman, Sterne, Kessler & Goldstein

[57] ABSTRACT

Peptides of the formula $R^1$-His-Asp-Glu-Ala-R wherein $R^1$ is Ala-Gln, and R is a polypeptide residue with up to 50 amino acid residues, and wherein one, more or all of the amino acid residues in $R^1$ and/or R independently may be omitted, can be used to augment cell mediated cytotoxicity and thereby to treat cancers and viral infections. These peptides may be prepared by proteolytic digestion of *Staphylococcus aureus* protein A, as well as by protein synthesis, recombinant DNA methods or any other methods known in the art.

22 Claims, 3 Drawing Sheets

Ala-Gln-His-Asp-Glu-Ala-Gln-Gln-Asn-Ala-Phe-Tyr-Gln-Val-Leu-Asn-Met-Pro-Asn-Leu-Asn-Ala-Asp-Gln-Arg-
5                             10                            15                            20                            25

Asn-Gly-Phe-Ile-Gln-Ser-Leu-Lys-Asp-Asp-Pro-Ser-Gln-Ser-Ala-Asn-Val-Leu-Gly-Glu-Ala-Gln-Lys-Leu-Asn-
30                            35                            40                            45                            50

Asp-Ser-Gln-Ala-Pro-Lys
55

FIG. 1

PEPTIDES AND COMPOSITIONS

BACKGROUND OF THE INVENTION

1. Field of the Invention

The present invention relates generally to novel peptides of formula I R$^1$-His-Asp-Glu-Ala-R, wherein R$^1$ is Ala-Gln and R is Gln-Gln-Asn-Ala-Phe-Tyr-Gln-Val-Leu-Asn-Met-Pro-Asn-Leu-Asn-Ala-Asp-Gln-Arg-Asn-Gly-Phe-Ile-Gln-Ser-Leu-Lys-Asp-Asp-Pro-Ser-Gln-Ser-Ala-Asn-Val-Leu-Gly-Glu-Ala-Gln-Lys-Leu-Asn-Asp-Ser-Gln-Ala-Pro-Lys and wherein at least one, more or all of the amino acid residues in R$^1$, R, or both is omitted; and physiologically compatible salts or esters thereof. These peptides exhibit interesting and surprising pharmacological properties in that they possess the ability to augment cell-mediated cytotoxy. The present invention therefore also relates to pharmaceutical compositions containing at least one of these peptides, their use as a medicament, e.g. an anticancer or antiviral agent, and methods for augmenting cell-mediated cytotoxicity in humans and other mammals.

In the following specification and claims the nomenclature used herein complies with that stated in J.Biol.Chem 247 (1972), 977 et seq.

2. Brief Description of the Background Art

Cancers and viral infections are serious conditions and until now no medicament has been found which can be used against all cancers or viral infections without side effects.

Natural killing (hereinafter NK) and antibody-dependent cellular cytotoxicity (hereinafter ADCC) are known examples of immunological defense mechanisms against cancer and viral infections. Several studies have indicated the relation between these types of cellular cytotoxic reactions and defense mechanisms against cancer as well as against viral infections. Therefore, stimulation of NK- and/or ADCC-activity as well as other mechanisms of cellular cytotoxicity (hereinafter collectively designated cellular killing (K-cell activity)) in vivo is believed to be of great relevance for the treatment of cancers and viral infections.

It has been demonstrated that one group of proteins, i.e. the interferons, stimulates these types of reactions. It is also known that certain other peptides and proteins stimulate K-cell activities. The lymphokine interleukin-2 has been indicated as particularly important for the stimulation of K-cell activity, and the augmentation of K-cell activity by lymphokines after stimulation for 3-5 days is often referred to as lymphokine activated killing (hereinafter LAK) and stimulated cells are referred to as lymphokine activated killer cells (hereinafter LAK-cells).

It is known that protein A from Staphylococcus aureus stimulates K-cell activities.

It is further known that S. aureus protein A (hereinafter SpA) has a number of other immunologic properties, including activation of the complement system, polyclonal stimulation of B- and T-lymphocytes, polyclonal activation of antibody synthesis and interferon induction.

These properties of SpA have led to a great deal of interest in the use of SpA as an immunologic reagent, and it is most desirable to find a way to exploit the useful properties of SpA without triggering the more adverse properties of this protein.

SpA cannot be employed directly in vivo since it may cause hypersensitive reactions (probably due to its binding to the Fc part of immunoglobulins with subsequent activation of complement etc.). Various preparations of the complete SpA molecule have, however, been utilized either for extracorporeal large-scale plasma adsorption (J. Balint jr. et al.: Cancer Research 44 (1984), 734–743), which was interpreted in terms of interaction with immunoglobulins in immune complexes, or for intravenous infusion in animals (H.D. Harper et al.: Cancer 55 (1985), 1863–1867) with beneficial results.

Protein A from S. aureus is a protein of which the NH$_2$-terminal part contains five homologous units comprising from 56 to 61 amino acids each, and the COOH-terminal part contains several repeats of an octapeptide (cf. Uhlén M. et al.: J.Biol.Chem. 259, 3 (1984), 1695–1702).

The five homologous regions in the N-terminal part are usually designated E, D, A, B, and C regions, and the C-terminal part is designated the X region.

The structure of SpA has been extensively studied and is described in a number of publications such as WO No. 8400773, WO No. 8400774, WO No. 840310 all to Pharmacia AB, and EP No. A2 107,509 to Repligen Corp. whereto reference is made.

The results obtained in studies performed by J. Sjödahl and G. Möller (Scand.J.Immunol. 10 (1979), 593–596) and Olinescu et al. (Immunol.Letters 6 (1983), 231–237) have been interpreted as indicating that the active part of the SpA molecule should be in the so-called X region, the C-terminally located portion of the molecule.

SUMMARY OF THE INVENTION

It has now, surprisingly, been found that peptides of formula I below have K-cell stimulating activity. A number of compounds of formula I have been identified from proteolytic cleavage of SpA and isolation of fragments that show no or low binding to immunoglobulins (i.e. they are substantially devoid of immunoglobulin cross-linking activity). These fragments have been shown to have K-cell stimulating activity in vitro against both NK-sensitive and insensitive target cells.

As indicated above the peptides of this invention may be derived from SpA as fragments consisting of a continous part of the amino acid sequence of the so-called region E, (cf. Uhlén M. et al.: J.Biol.Chem. 259, 3 (1984), 1695–1702), which fragments comprise from 4 and up to 55 amino acid residues from the entire sequence of region E.

In one aspect the invention thus relates to peptides of the general formula I

R$^1$-His-Asp-Glu-Ala-R  (I)

wherein R$^1$ is Ala-Gln and R is

Gln-Gln-Asn-Ala-Phe-Tyr-Gln-Val-Leu-Asn-Met-Pro-Asn-Leu-Asn-Ala-Asp-Gln-Arg-Asn-Gly-Phe-Ile-Gln-Ser-Leu-Lys-Asp- Asp-Pro-Ser-Gln-Ser-Ala-Asn-Val-Leu-Gly-Glu-Ala-Gln-Lys-Leu-Asn-Asp-Ser-Gln-Ala-Pro-Lys and wherein at least one, more or all of the amino acid residues in R$^1$, R, or both is omitted; and physiologically compatible salts or esters thereof.

A subclass of peptides according to the invention is peptides of formula I wherein R$^1$ and R are defined as above, and wherein the only part of $R^1$ that is omitted constitutes a continuous part of the amino acid sequence of $R^1$ from the N-terminal end, and the only part of R that is omitted constitutes a continuous part of the amino acid sequence of R from the C-terminal end.

As examples of specific and preferred peptides of formula I the following can be mentioned Ala-Gln-His-Asp-Glu-Ala-Gln-Gln-Asn-Ala-Phe-Tyr-Gln-Val-Leu- Asn-Met-Pro-Asn-Leu-Asn-Ala-Asp-Gln-Arg-Asn-Gly-Phe-Ile-Gln- Ser-Leu-Lys-Asp-Asp-Pro-Ser-Gln-Ser-Ala-Asn-Val-Leu-Gly-Glu- Ala-Gln-Lys-Leu-Asn-Asp-Ser-Gln-Ala-Pro, pX-3' (corresponding to the 55 N-terminal amino acid residues in region of SpA), Ala-Gln-His-Asp-Glu-Ala-Gln-Gln-Asn-Ala-Phe-Tyr-Gln-Val-Leu- Asn-Met-Pro-Asn-Leu-Asn-Ala-Asp-Gln-Arg, pX-1' (corresponding to the first 25 amino acid residues in region E), Ala-Gln-His-Asp-Glu-Ala-Gln-Gln-Asn-Ala-Phe-Tyr-Gln-Val-Leu- Asn-Met-Pro-Asn-Leu, pX-2' (corresponding to the first 20 amino acid residues in region E), Gln-His-Asp-Glu-Ala-Gln-Gln-Asn-Ala-Phe-Tyr-Gln-Val-Leu-Asn- Met-Pro-Asn-Leu, pX-4' (corresponding to amino acid residues 2 to 20 in region E), and His-Asp-Glu-Ala-Gln-Gln-Asn-Ala-Phe-Tyr-Gln-Val-Leu-Asn-Met- Pro-Asn-Leu, pX-5' (corresponding to amino acids 3 to 20 in region E).

In another aspect the invention relates to pharmaceutical compositions containing at least one peptide of the general formula I in combination with an inert carrier or excipient.

In a further aspect the invention relates to compositions useful for augmenting K-cell activity in animal cells which comprise a peptide with an amino acid sequence corresponding to the E-region of SpA or fragments thereof, said peptide characterized further in that it is substantially devoid of immunoglobulin binding activity, and physiologically acceptable salts or esters thereof, together with a physiologically acceptable carrier.

The compositions of the invention may further contain one or more other active substances, e.g. interferons, lymphokines and/or monokines.

In a further aspect the invention relates to a method of combating conditions of cancers or viral infections in mammals including humans by administering a therapeutically effective amount of at least one of said compositions to a subject suffering from cancer or a viral infection.

In a still further aspect the invention relates to the use of a peptide of the formula I or a peptide with an amino acid sequence corresponding to the E region of SpA or fragments thereof as a medicament for administration to mammals, including humans.

In yet another aspect the invention relates to a method of augmenting cell mediated cytotoxicity in mammals by administering an effective amount of at least one peptide of formula I in a quantity sufficient to augment K-cell activity.

BRIEF DESCRIPTION OF THE DRAWINGS

FIG. 1 shows the amino acid sequences of the region E of protein A from *Staphylococcus aureus* strain 8325-4 (cf. Uhlén et al., above)

DETAILED DESCRIPTION OF THE INVENTION

Figure 2:
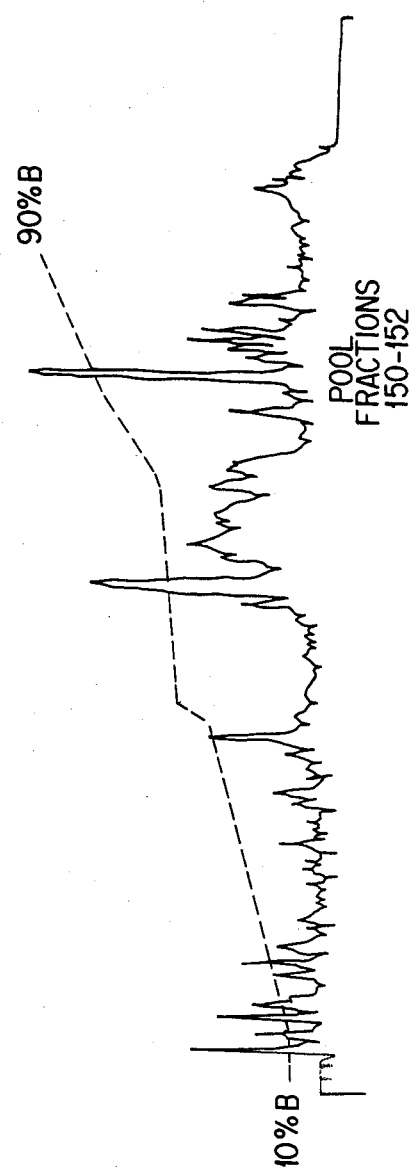
FIG. 2 shows the elution pattern obtained in the isolation of a peptide according to the invention.

The invention is based on the surprising observation that apparently the ability of SpA to augment cell mediated cytotoxicity resides in the E region or fragments thereof.

Further it has also surprisingly been found that the E region or fragments thereof have no or low affinity to immunoglobulins whereby activation of complement is substantially eliminated.

All these fragments in question comprise the amino acid residues His-Asp-Glu-Ala.

In FIG. 1 the amino acid sequence of region E is shown with markers indicating the preferred peptides of the invention.

The present invention provides a number of peptides which may be derived from the amino acid sequence of the E region of SpA. One of these was derived from plasmin digestion of SpA and the amino acid sequence defined as follows:

Ala—Gln—His—Asp—Glu—Ala—Gln—Gln—Asn—Ala—Phe—
              5                              10

—Tyr—Gln—Val—Leu—Asn—Met—Pro—Asn—Leu—
     15                          20

—Asn—Ala—Asp—Gln—Arg (pX-1')
                                25

Another was synthesized as:

Ala—Gln—His—Asp—Glu—Ala—Gln—Gln—Asn—Ala—Phe—
              5                              10

—Tyr—Gln—Val—Leu—Asn—Met—Pro—Asn—Leu (pX-2')
     15                              20

Both these peptides of the invention were tested and observed to augment cell mediated cytotoxicity in in vitro assays for the augmentation of K-cell activity.

The amino acid sequences of pX-1' and pX-2' correspond to those of the first 25 and 20 amino acid residues, respectively, in SpA, corresponding to the N-terminal part of region E, which region comprises the first 56 amino acids of SpA.

The peptides of the invention may be synthesized by any method known to those skilled in the art. A summary of such techniques may be found in J.M. Stewart and J.D. Young, Solid Phase Peptide Synthesis, W.H. Freeman, San Francisco, 1969 and J. Meienhofer, Hormonal Proteins and Peptides, Vol. 2, (1973), p. 46, Academic Press, New York, for solid phase synthesis, and in E. Schroder and K. Lubke, The Peptides, Vol. 1, (1965), Academic Press, New York, for classical solution synthesis.

In general these methods comprise the sequential addition of one or more amino acids, or suitably protected amino acids, to a growing peptide chain. Normally, either the amino or the carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

In addition the subject polypeptides may be prepared by recombinant DNA technology, for example by modification and utilization of a part of the DNA sequences coding for *S. aureus* protein A.

The peptides of the invention may also be produced by proteolytic or chemical cleavage of SpA and subsequent fractionation and isolation of the SpA fragments.

For the digestion various proteolytic enzymes may be used such as trypsin, plasmin, *Armillaria mellea* protease or clostripain, chymotrypsin, carboxypeptidases or *S. aureus* V8 protease. For chemical cleavage CNBr, acids or bases could be used.

The isolation of the peptides may be performed by any suitable method known to those skilled in the art, such as by High Pressure Liquid Chromatography (HPLC).

Peptides of formula I or peptides with an amino acid sequence corresponding to the E-region of SpA or fragments thereof are converted into pharmaceutical compositions and administered, preferably to humans, in analogy with known methods. Said peptides and salts or esters thereof can be administered perorally, topically, rectally, vaginally, intraveneously, intramuscularily, intrathecally or subcutaneously at dosages in the range of from about 1 to 1000 μg/kg body weight, although a lower or higher dosage may be administered. The required dosage will depend on the severity of the condition of the patient, the peptide used, the mode of administration and the duration of treatment.

The compositions may be formulated in the form of slow-release or depot preparations.

For the purpose of parenteral administration, the said peptides are dissolved in sterile, isotonic saline solutions.

As examples of salts of the above mentioned peptides, for example sodium, potassium, magnesium, calcium and zinc salts and acid addition salts with organic or inorganic acids such as formic acid, methanesulphonic acid, hydrochloric acid and sulphoric acid can be mentioned. Preferred salts of the said peptides are physiologically and pharmaceutically acceptable salts.

Over and above one of said peptides or a salt or ester thereof the pharmaceutical compositions may comprise a pharmaceutically acceptable carrier, diluent, preferably isotonic saline solutions, and/or excipient.

The present invention will be described in greater detail in the following examples, which in no way are intended to limit the scope of the invention as set forth in the appended claims.

EXAMPLE 1

Preparation of peptides by proteolytic cleavage of SpA

(a) Digestion with Plasmin 15 mg of purified SpA from Pharmacia, Uppsala, Sweden, were dissolved in 600 μl of 0.1 M ammonium formate (pH 7.5) and 600 μl of plasmin (corresponding to 14 CU (casein units)) dissolved in the same buffer was added. The mixture was incubated at 37° C. for 205 minutes. The reaction was terminated by adding aprotinin coupled to Sepharose ® 4B followed by a further 15 minutes of incubation at room temperature. Subsequently, the reaction mixture was centrifuged, and the supernatant was drawn out by suction. 1.0 ml of 0.1 M ammonium formate was added to the pellet (containing immobilized aprotinin as well as remaining reaction mixture), the sample was mixed and centrifuged, and the supernatant was drawn out by suction. The latter procedure was repeated twice.

Finally all the supernatants were combined and lyophilized repeatedly.

(b) Purification.

The peptides from above were purified by high pressure liquid chromatography (HPLC) on a reverse phase column (Nucleosil ® 5$C_{18}$) using the following equipment: 2 LKB 2150 HPLC pumps, LKB 2151 variable wavelength monitor, LKB 2152 HPLC controller, LKB 2220 recording integrator and LKB Superrac.

The purification was performed as follows:
Buffer A: 0,02 M ammonium formate (pH 6.5); buffer B: 40% 0.05 M ammonium formate (pH 6.5) and 60% ethanol; flow rate: 0.5 ml/min; fraction volume: 0.25 ml.

The material in fractions 150–152 was selected for characterization.

The results of the HPLC purification are shown in FIG. 2, wherein the selected fractions are indicated.

The product contained two peptides that were sequenced according to the following protocol:

Edman degradations of the peptides were performed with an Applied Biosystems model 470A gas phase sequencer as described (R.M. Hewick, M.W. Hunkapiller, L.E. Hood and W.J. Dreyer: J.Biol.Chem. 256 (1981) 7990–7997; M.W. Hunkapiller, R.M. Hewick, W.J. Dreyer and L.E. Hood: Methods Enzymol. 91 (1983) 399–413) with several modifications. A fourth solvent (Sl = n-heptane) was included for washing the filter for 30 seconds after coupling with phenylisothiocyanate (PITC). In order to obtain the methylated derivatives of Asp and Glu, the conversion of amino acid anilinothiazolinones to phenylthiohydantoins was carried out with 1 N methanolic HCl instead of 25% trifluoroacetic acid (TFA). The sequencer program was adjusted to this reagent, as shorter drying periods were necessary. The phenylthiohydantoine amino acids (PTH-a.a.) were dissolved in approximately 0.25 ml of methanol and dried in a Savant vacuum centrifuge for 10 min at 45° C. Dried PTH-a.a. were redissolved in 0.025 ml of methanol containing methylthiohydantoin-(MTH)-tyrosine as internal standard. The PTH-a.a. were identified and quantified by reverse phase HPLC on a 25 cm×0.46 cm IBM cyano column equipped with a 5 cm×0.46 cm Permaphase ® ETH cyano guard column (DuPont) (M.W. Hunkapiller and L.E. Hood: Methods Enzymol. 91 (1983) 486 Hunkapiller 493) in a Hewlett Packard Liquid Chromatograph Model 1084B equipped with a variable UV detector Model 79875.

The A solvent was 16 mM sodium acetate, pH 5.60, and the B solvent was acetonitrile/methanol, 9:1 (v/v). The column was equilibrated with 15% of B and eluted with a linear gradient of 15% - 51.4% B for 0–15.30 min. The PTH-a.a. were detected at 263 nm at 1.5 mAUFS (Absorption Unit Full Scale).

The amino acid sequence data are shown in table 1 below:

TABLE 1

Sequence analysis of peptide pool
Sample: Fraction 150-152 (see FIG. 2)
Average repetitive yield: 95.7%

| Cyclus No. | PTH-a.a. | Amount (pmol) | PTH-a.a. | Amount (pmol) |
|---|---|---|---|---|
| 1 | Asp | 391 | Ala | 853 |
| 2* | Gln | (1500) | Gln | (750) |
| 3 | Gln | 1405 | His | 266 |
| 4 | Ser | 59 | Asp | 168 |
| 5 | Ala | 870 | Glu | 424 |
| 6 | Phe | 715 | Ala | 505 |
| 7 | Tyr | 1062 | Gln | 749 |
| 8* | Glu | (850) | Gln | (425) |
| 9 | Ile | 746 | Asn | 665 |
| 10 | Leu | 624 | Ala | 360 |
| 11 | Asn | 531 | Phe | 298 |
| 12 | Met | 575 | Tyr | 454 |
| 13 | Pro | 519 | Gln | 560 |
| 14 | Asn | 820 | Val | 383 |
| 15* | Leu | (483) | Leu | (241) |
| 16* | Asn | (737) | Asn | (368) |
| 17 | Glu | 198 | Met | 323 |
| 18 | Ala | 288 | Pro | 176 |
| 19 | Gln | 540 | Asn | 419 |
| 20 | Arg | 140 | Leu | 392 |
| 21 | | | $Y_1$ | — |
| 22 | | | Ala | 280 |
| 23 | | | $Y_2$ | — |
| 24 | | | Gln | 79 |
| 25 | | | Arg | 177 |

*Here the same amino acid residue appears in both peptides, the amount found is therefore shared proportionally between the peptides.

It appears from table 1 that the purified pooled material contains a mixture of two peptides. The unidentified amino acid residues $Y_1$ and $Y_2$ can be assigned as Asn and Asp, respectively, by comparing the sequence with the sequence of protein A from *S. aureus* (Uhlen et al., above).

The product thus consist of 33% of a peptide, pX-1', of formula I with $R^1$ being Ala-Gln, and R being Gln-Gln-Asn- Ala-Phe-Tyr-Gln-Val-Leu-Asn-Met-Pro-Asn-Leu-Asn-Ala-Asp-Gln-Arg (III) corresponding to the first 25 amino acid residues in the N-terminal part of SpA, which are also the first 25 amino acid residues in the N-terminal part of region E; and 67% of a peptide corresponding to amino acid residues 11 to 30 in region D.

The product was shown to have K-cell activity augmenting activity in the assay procedures detailed below.

EXAMPLE 2

Preparation of peptide mixtures by proteolytic cleavage of SpA (a) Digestion with plasmin 150 μg purified SpA were digested with 0.3 CU (casein units) plasmin (KABI) at 37° C. for 60 min.

The reaction was terminated by adding aprotinin coupled to Sepharose ® 4B and incubation for 15 minutes at room temperature. The supernatants were removed after centrifugation and used in the experiments below.

(b) Analysis of K cell stimulation activity

Figure 3:
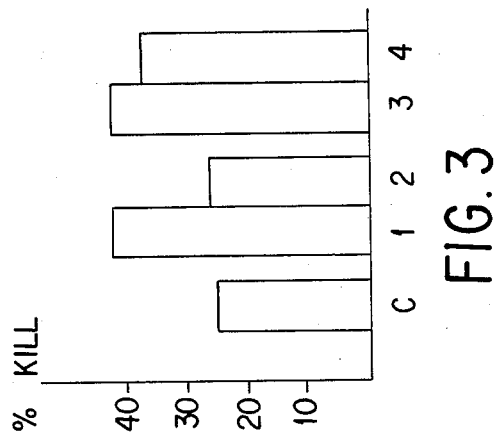
FIG. 3 shows the results of a comparative test between SpA and non IgG binding fragments.

To evaluate the importance of non-Fc binding peptides in in vitro stimulation of K cell activity, the proteolytic digests from above (corresponding to 8 μg SpA) were incubated with human IgG coupled to Sepharose 4B or with control Sepharose 4B for 30 minutes at room temperature. Purified SpA was incubated under identical conditions as control. The reaction mixtures were centrifuged and the supernatants were used directly in the K cell assay as detailed below. Thus normal peripheral blood leukocytes (PBL) were incubated with (1) SpA absorbed with IgG-Sepharose 4B, (2) SpA absorbed with control-Sepharose 4B, (3) plasmin-digested SpA absorbed with IgG Sepharose 4B, (4) plasmin-digested SpA absorbed with control-Sepharose 4B. PBL incubated with medium alone served as controls. The results expressed as Kill % are given in FIG. 3. It appears that it is possible by proteolytic cleavage of purified SpA to obtain peptides with no or low IgG binding, but with K cell stimulation activity.

EXAMPLE 3

Synthetic preparation of peptides pX-2'

(a) Ala-Gln-His-Asp-Glu-Ala-Gln-Gln-Asn-Ala-Phe-Tyr- Gln-Val-Leu-Asn-Met-Pro-Asn-Leu, pX-2', corresponding to the first 20 amino acid residues of the N-terminal part of region E was prepared synthetically as indicated above.

pX-2' showed K-cell activity augmenting activity in the assay procedures below.

Assay procedures

K-cell activity is here defined as the increase in cell mediated cytotoxicity of normal peripheral blood leukocytes (PBL) against tumor derived target cells. PBL were isolated by the Böyum method (Scand.J.Clin.Lab.Invest. 22 (1968) 77) by centrifugation of heparinized blood from healthy donors on Ficoll-Hypaque ® (Pharmacia, Uppsala, Sweden). In many experiments adherent cells were removed by incubating PBL in sterile glass bottles at 37° C. for 1 to 2 hours. As target cells the NK-sensitive K562 (C.B. and B.B. Lozzio, J.Nat.Cancer Inst. 50 (1973) 535–538) as well as the relatively NK-resistant Daudi (E. Klein et al., Cancer Res. 28 (1968) 1300–1310) and Raji (R.J.V. Pulvertaft, J.Clin.Pathol. 18 (1965) 261–273) cell lines were used for the peptides obtained by proteolytic digestion of SpA, while only Raji and Daudi cell lines were used for the synthetic peptides.

The cell lines were kept in culture in RPMI 1640 (Gibco, Paisley, Scotland, Cat. No. 041-1875) to which was added fetal calf serum (10% v/v) (FCS) as well as penicillin (100 IU/ml) and streptomycin (100 μg/ml) at 37° C. and carbon dioxide in air.

The target cells were labelled with $^{51}Cr$ (New England Nuclear, Dreieich, West Germany).

K-cell assay

PBL were incubated with purified peptides or with SpA for 24 h at 37° C. with 6% $CO_2$ in air. The medium used was RPMI 1640 to which was added 10% of FCS, penicillin (100 IU/ml) and streptomycin (100 μg/ml). After incubation, the cell density was adjusted and the cells were distributed in round-bottom microtiter plates (NUNC, Roskilde, Denmark). $^{51}Cr$-labeled K562 target cells were added to a desired ratio between effector (E) and target (T) cells (E/T 10:1). After a further 4 hours of incubation at 37° C. with 6% $CO_2$ in air, the plates were placed on a Titertek ® microtiter plate shaker (Flow Laboratories Ltd., Ayrshire, Scotland). The microtiter plates were centrifuged and known volumes of the supernatant removed by suction and counted $^{51}Cr$-sample). As maximum value ($^{51}Cr$-max), use was made of the supernatant from K562 incubated with saponin. The spontaneous release of $^{51}Cr$ ($^{51}Cr$-spont) was measured by incubating $^{51}Cr$-K562 without effector cells. The specific percentage of killing (Kill %) was calculated using the following equation (all values referring to $^{51}Cr$ in directly comparable supernatants):

Kill %: 100($^{51}Cr$-sample - Cr-max$^{51}Cr$-sample - $^{51}Cr$-spont)/($^{51}Cr$-may /$^{51}Cr$-spont)

The method employed was practically the same as above for Daudi and Raji targets. The only substantial difference was that no preincubation was performed prior to addition of the $^{51}Cr$-labelled target cells, and the complete incubation of effector and target cells was done in 24 hours. The Kill % was calculated as described above.

The above assays for the activity of the peptides were used for the final characterization as well as in several screening tests. The screening tests were performed directly on fractions from the different steps of the HPLC-purification, and in most instances the fractions were lyophilized first. Two different target cells (K562 and Daudi) were used in the screening tests. Only those fractions that were positive in both test systems were used in the further purification and characterization.

Short-term test. NK-like activity $4 \times 10^5$ monocyte-depleted mononuclear cells were incubated with $4 \times 10^4$ $^{51}Cr$-labelled Raji cells. Total volume: 800 μl. To this was added 1.5, 6, 25 or 100 μg of peptide per ml, respectively. Controls were unstimulated effector cells +$^{51}Cr$-labelled Raji and effector cells stimulated with SpA (20 μg/ml) (in duplicate). After 2 hours of incubation $3 \times 200$ μl were taken out for incubation in round-bottom microtiter trays. Incubation was carried out at 37° C., 7% $CO_2$, 18h.

Long-term test. LAK-like activity $6 \times 10^6$ monocyte-depleted mononuclear cells were incubated in 6 ml RPMI 1640 +5% FCS, penicillin (100 IU/ml) and streptomycin (100 μg/ml) in vertically suspended Falcon flasks (Falcon Plastics, Oxnard, CA., USA, Cat. No. 3013). As in the short-term test, 1.5, 6, 25 or 100 μg peptide per ml, respectively, were added. Controls: unstimulated effector cells and effector cells +SpA (20 μg/ml). Incubation for 72 h at 37° C., 7% $CO_2$. The cells were counted, density adjusted and the cells incubated together with $^{51}Cr$-labelled Raji and Daudi target cells. E/T ratios were: 10:1 and 20:1. In the Daudi test the incubation lasted 16 hours, in the Raji test it was 18 hours (round-bottom microtiter plates, as above).

The results of the above assays are shown in the following table 2 for the SpA peptides and in table 3 for the synthetic peptides.

TABLE 2

Natural killer (NK)-like activity induced by incubation of peripheral blood lymphocytes (PBL) with peptides isolated from proteolytic digests of SpA or intact SpA.

|  |  | % kill* | |
|---|---|---|---|
|  |  | Raji | Daudi |
| Control |  | 15 | 46 |
| Pool (pX-1'**) approx. | 100 pmol/ml | 27 | 75 |
|  | 20 pmol/ml | 27 | 72 |
|  | 4 pmol/ml | 24 | 68 |
| Protein A | 10 μg/ml (250 pmol/ml) | 46 | 77 |
|  | 5 μg/ml (125 pmol/ml) | 46 | 71 |
|  | 5 μg/ml (12.5 pmol/ml) | 31 | 66 |

*E/T ratio = effector to target cell ratio = 10:1
**Concentrations of pX-1' are estimates.

TABLE 3

Effect of synthetic peptide, pX-2', on the NK- and LAK-like activities of PBL.

|  | Stimulation index* | | | |
|---|---|---|---|---|
|  | Short-term assay (NK-like activity) | Long-term assay (LAK-like activity) | | |
| Targets | Raji | Raji | | Daudi |
| E/T** ratio | 10:1 | 10:1 | 20:1 | 10:1 | 20:1 |
| 100 μg/ml | 0.79 | n.d.*** | n.d. | n.d. | n.d. |
| 25 μg/ml | 1.15 | 1.41 | 1.48 | 1.15 | 1.07 |
| 6 μg/ml | 1.23 | 1.02 | 1.12 | 1.05 | 1.03 |
| 1.5 μg/ml | 0.97 | 0.94 | 0.97 | 1.00 | 0.99 |
| SpA 20 μg/ml | 1.08 | 1.51 | 1.17 | 1.19 | 1.07 |

*(activity of sample)/(activity of control)
**E/T ratio = effector to target cell ratio
***not done From table 2 it is seen that an estimated amount of 100 pmol/ml of material (calculated on the basis of pX-1') showed the same NK-cell stimulating activity as 125 to 250 pmol/ml of intact SpA using Daudi cells as targets, while its activity against Raji cells was somewhat lower.

From table 3 it is seen that pX-2' has an activity in all the tests that is equal to the activity of intact SpA.

Activation of Complement

In order to investigate the influence of the compounds of the invention on the complement system a test was performed in which the generation of the complement split product C5a was used as a measure of the activation of complement.

The test was performed by incubating normal human serum with SpA (Pharmacia Fine Chemicals Upsala, Sweden) or pX-2' for 60 minutes. Aliquots were taken after 0, 30, and 60 minutes and the generated C5a des-Arg was quantitated by a commercial RIA-kit (Upjohn Company, Kalamazoo, MI).

Figure 4:
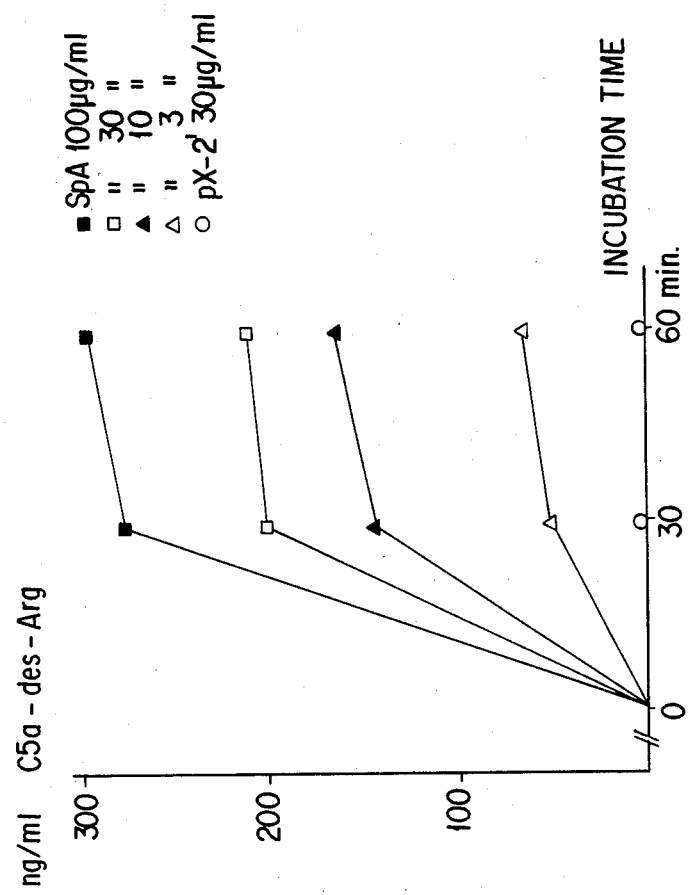
FIG. 4 shows the results of a test for complement activation by SpA and a peptide according to the invention.

The results are shown in FIG. 4 and it is clearly seen that pX-2' is completely devoid of any activating effect, while SpA has a considerable C5a generating capacity, which dose-dependently increased the formation of C5a-des-Arg (the stable metabolite of C5a).

Guinea Pig Model

A further test was performed wherein the ability of peptides of the invention and SpA to induce an anaphylactoid-like reaction when administered intravenously into anaesthesized and artificially ventilated guinea pigs was investigated.

Guinea pigs of Dunkin-Hartley strain (ca. 500 g) were anaesthesized with sodium pentobarbital and were surgically prepared with a catheter in the jugular vein for drug infusion. The blood pressure was registered from a carotid artery. The animals were artificially ventilated by a Harvard small animal respirator at a cycle of 38 insufflations per min. and a volume of 1 ml per 100 g animal.

Protein A and pX-2' was administered intravenously, and it was found that protein A dose-dependently (10-100 μg/ml i.v.) produced an anaphylactoid-like reaction indicated by an initial bronchoconstriction and hypertension (later hypotension) subsequent to intravenous administration, while pX-2' did not induce any such reaction.

EXAMPLE 4

A preparation for parenteral administration, containing 1 mg of a peptide of formula I per ml, may be prepared as follows:

1 g of a peptide of formula I and 99 g of lactose are dissolved in 1 liter of distilled water and the pH is adjusted to about 7.0. The solution is sterile filtered. The sterile solution is filled in 10 ml vials in such a way that each vial contains 1.0 ml of the solution. The solutions are lyophilized and the vials are sealed under aseptic conditions.

The preparation in any single vial is to be dissolved in 1.0 ml of sterile, isotonic saline solution before administration.

EXAMPLE 5

Rectal suppositories are prepared by mixing 1 mg of a formula peptide with 4 g of cocoa butter.

We claim:

1. A peptide of the general formula I

R$^1$-His-Asp-Glu-Ala-R  (I)

and physiologically compatible salts or esters thereof, wherein R$^1$ is Ala-Gln and R is
   Gln-Gln-Asn-Ala-Phe-Tyr-Gln-Val-Leu-Asn-Met-Pro-Asn-Leu-Asn-Ala-Asp-Gln-Arg-Asn-Gly-Phe-Ile-Gln-Ser-Leu-Lys-Asp-Asp-Pro-Ser-Gln-Ser-Ala-Asn-Val-Leu-Gly-Glu-Ala-Gln-Lys-Leu-Asn-Asp-Ser-
and wherein at least one or more of the amino acid residues in R$^1$, R, or both is omitted, and wherein the only part of R$^1$ that is omitted constitutes a continuous part of the amino acid sequence of R$^1$ from the N-terminal end, and the only part of R that is omitted constitutes a continuous part of the amino acid sequence of R from the C-terminal end.

2. Peptides according to claim 1, wherein R$^1$ is defined as above, and R has the formula III Gln-Gln-Asn-Ala-Phe-Tyr-Gln-Val-Leu-Asn-Met-Pro-Asn-Leu-Asn-Ala-Asp-Gln-Arg  (III)

and physiologically compatible salts or esters thereof.

3. A peptide according to claim 1, wherein R$^1$ is defined as above, and R has the formula V Gln-Gln-Asn-Ala-Phe-Tyr-Gln-Val-Leu-Asn-Met-Pro-Asn-Leu  (V)

and physiologically compatible salts or esters thereof.

4. A peptide according to claim 1, wherein R$^1$ is defined as above, and R has the formula VI Gln-Gln-Asn-Ala-Phe-Tyr-Gln-Val-Leu-Asn-Met-Pro-Asn  (VI)

and physiologically compatible salts or esters thereof.

5. A peptide according to claim 1, wherein R$^1$ is defined as above, and R has the formula VII Gln-Gln-Asn-Ala-Phe-Tyr-Gln-Val-Leu-Asn-Met-Pro  (VII)

and physiologically compatible salts or esters thereof.

6. A peptide according to claim 1, wherein R$^1$ is defined as above, and R has the formula VIII Gln-Gln-Asn-Ala-Phe-Tyr-Gln-Val-Leu-Asn-Met  (VIII)

and physiologically compatible salts or esters thereof.

7. A peptide according to claim 1, wherein R$^1$ is defined as above, and R has the formula IX Gln-Gln-Asn-Ala-Phe-Tyr-Gln-Val-Leu-Asn  (IX)

and physiologically compatible salts or esters thereof.

8. A peptide according to claim 1, wherein R$^1$ is defined as above, and R has the formula X Gln-Gln-Asn-Ala-Phe-Tyr-Gln-Val-Leu  (X)

and physiologically compatible salts or esters thereof.

9. A peptide according to claim 1, wherein R$^1$ is defined as above, and R has the formula XI Gln-Gln-Asn-Ala-Phe-Tyr-Gln-Val  (XI)

and physiologically compatible salts or esters thereof.

10. A peptide according to claim 1, wherein R$^1$ is defined as above, and R has the formula XII Gln-Gln-Asn-Ala-Phe-Tyr-Gln  (XII)

and physiologically compatible salts or esters thereof.

11. A peptide according to claim 1, wherein R$^1$ is defined as above, and R has the formula XIII Gln-Gln-Asn-Ala-Phe-Tyr  (XIII)

and physiologically compatible salts or esters thereof.

12. A peptide according to claim 1, wherein R$^1$ is defined as above, and R has the formula XIV Gln-Gln-Asn-Ala-Phe  (XIV)

and physiologically compatible salts or esters thereof.

13. A peptide according to claim 1, wherein R$^1$ is defined as above, and R has the formula XV Gln-Gln-Asn-Ala  (XV)

and physiologically compatible salts or esters thereof.

14. A peptide according to claim 1, wherein R$^1$ is defined as above, and R has the formula XVI Gln-Gln-Asn  (XVI)

and physiologically compatible salts or esters thereof.

15. A peptide according to claim 1, wherein $R^1$ is defined as above, and R is Gln-Gln, and physiologically compatible salts or esters thereof.

16. A peptide according to claim 1, wherein $R^1$ is defined as above, and R is Gln, and physiologically compatible salts or esters thereof.

17. A pharmaceutical composition which contains at least one peptide or a salt or ester thereof according to claim 1, in combination with a pharmaceutically acceptable carrier or exipient.

18. A pharmaceutical composition according to claim 17, characterized in that it further comprises one or more other active substances selected from the group consisting of interferon, lymphokine and monokine.

19. A method of treating disorders in mammals, characterized in administering to a mammal a medicament comprising a peptide or a pharmaceutical composition according to any of claims 1, 17, or 18.

20. A method of augmenting cell mediated cytotoxicity in mammals, characterized in administering to a mammal an effective amount of at least one peptide or pharmaceutical composition according to any of the claims 1 or 2 to augment cell mediated cytotoxicity in a subject.

21. A method for the treatment of conditions of cancer in mammals, characterized in administering to a subject suffering from cancer a therapeutically effective amount of a peptide or a pharmaceutical composition according to any of the claims 1, 17 or 18.

22. A method for the treatment of viral infections in mammals, characterized in administering to a subject suffering from a viral infection a therapeutically effective amount of a peptide or a pharmaceutical composition according to any of the claims 1 or 2.

* * * * *